United States Patent
Shi et al.

(10) Patent No.: US 9,713,586 B2
(45) Date of Patent: Jul. 25, 2017

(54) ORAL CARE COMPOSITION

(71) Applicant: COLGATE-PALMOLIVE COMPANY, New York, NY (US)

(72) Inventors: Manying Shi, Guangzhou (CN); Xiaojing Lv, Guangzhou (CN); Rolando Plata, Mumbai (IN); Zhuoxing Zhang, Guangzhou (CN)

(73) Assignee: Colgate-Palmolive Company, New York, NY (US)

(*) Notice: Subject to any disclaimer, the term of this patent is extended or adjusted under 35 U.S.C. 154(b) by 0 days.

(21) Appl. No.: 15/022,720

(22) PCT Filed: Sep. 17, 2013

(86) PCT No.: PCT/CN2013/083609
§ 371 (c)(1),
(2) Date: Mar. 17, 2016

(87) PCT Pub. No.: WO2015/039277
PCT Pub. Date: Mar. 26, 2015

(65) Prior Publication Data
US 2016/0228347 A1    Aug. 11, 2016

(51) Int. Cl.
*A61K 8/73* (2006.01)
*A61K 8/34* (2006.01)
*A61K 8/86* (2006.01)
*A61K 8/25* (2006.01)
*A61Q 11/00* (2006.01)

(52) U.S. Cl.
CPC ............. *A61K 8/733* (2013.01); *A61K 8/25* (2013.01); *A61K 8/345* (2013.01); *A61K 8/86* (2013.01); *A61Q 11/00* (2013.01); *A61K 2800/30* (2013.01); *A61K 2800/48* (2013.01); *A61K 2800/92* (2013.01)

(58) Field of Classification Search
None
See application file for complete search history.

(56) References Cited

U.S. PATENT DOCUMENTS

| | | | | |
|---|---|---|---|---|
| 4,298,383 A | * | 11/1981 | Joyce | B22F 3/001 419/36 |
| 4,401,648 A | * | 8/1983 | Piechota, Jr. | A61K 8/042 424/49 |
| 4,765,984 A | | 8/1988 | Vellekoop et al. | |
| 5,366,742 A | | 11/1994 | Tuason, Jr. et al. | |
| 5,482,932 A | * | 1/1996 | Thompson | A61L 26/0023 424/443 |
| 6,120,754 A | * | 9/2000 | Lee | A61K 8/24 424/49 |
| 2006/0280713 A1 | | 12/2006 | Malessa | |
| 2012/0315228 A1 | | 12/2012 | Deng et al. | |

FOREIGN PATENT DOCUMENTS

| | | | |
|---|---|---|---|
| CN | 102219938 | 10/2011 | |
| CN | WO 2012143220 A1 * | 10/2012 | ............... A61K 8/19 |
| EP | 0380254 | 8/1990 | |
| EP | 1453488 B1 | 10/2009 | |
| JP | 2009-120552 | 6/2009 | |
| KR | 20060021967 | 3/2006 | |
| WO | WO 96/11230 | 4/1996 | |
| WO | WO 2007/066837 | 6/2007 | |
| WO | WO 2012/152054 | 11/2012 | |

OTHER PUBLICATIONS

Sugar substitute—Wikipedia. Downloaded Jun. 8, 2016 from: https://en.wikipedia.org/wiki/Sugar_substitute.*
Polyethylene glycols (PEGs) from Mindfully.org (originally publication—Sheftel, VO. Indirect Food Additives and Polymers:Migration and Toxicology. Lewis 2000, pp. 1114-11116), downloaded Jun. 1, 2016 from: http://www.mindfully.org/Plastic/Polymers/Polyethylene-Glycols-PEGs.htm.*
Celine Sartori. The Characterisation of Alginate Systems for Biomedical Applications. Thesis submitted for the degree of Doctor of Philosophy, Brunel University, London, May, 1997, pp. 1-35 provided.*
Definition of "diluted" from "The Free Dictionary", downloaded Jun. 2, 2016, from the site: http://www.thefreedictionary.com/dilute.*
International Search Report and the Written Opinion of the International Searching Authority issued in International Patent Application PCT/CN2013/083609 mailed Jun. 27, 2014.

* cited by examiner

*Primary Examiner* — Frederick Krass
*Assistant Examiner* — Michael P Cohen

(57) ABSTRACT

An oral care composition comprising a diluted sodium calcium alginate gel, wherein the oral care composition is a toothpaste, a gel, a mouthwash or a mouthrinse.

25 Claims, No Drawings

ORAL CARE COMPOSITION

CROSS-REFERENCE TO RELATED PATENT APPLICATIONS

This application is a U.S. national stage application under 35 U.S.C. §371 of PCT Application No. PCT/CN2013/083609, filed Sep. 17, 2013, the entirety of which is incorporated herein by reference.

BACKGROUND

Alginate gum is a natural gum derived from seaweed (a rich natural resource). Alginate gum is a highly effective gelling and thickening agent and has been widely used in the food and pharmaceutical industries as such an agent. A commonly-used alginate gum is sodium alginate, which has a linear long chain structure. Aqueous solutions of sodium alginate at 1 wt. % are normally within viscosity range of from 100-1000 cps, they are colorless and as viscous fluid under room temperature.

However, disadvantages of sodium alginate for toothpaste applications include lack of structural property for a striped toothpaste and the viscosity/price tends not to deliver cost benefit.

Another type of alginate is calcium alginate. Calcium alginate can be formed by the addition of calcium ions (for example as an aqueous solution of $CaCl_2$ but normally together with chelator like EDTA used to slow down the cross-linking) to sodium alginate. Calcium alginate is water-insoluble.

It would be desirable to provide a rheology modifier which has a clear, colourless appearance when in aqueous solution, yet which still continually flows under an applied shear stress and viscosity, and which provides excellent thickening and structural effects.

SUMMARY

A first aspect of the present invention provides an oral care composition comprising a diluted sodium calcium alginate gel, wherein the oral care composition is a toothpaste, a gel, a mouthwash or a mouthrinse.

Optionally, the composition is a toothpaste or a gel.

Optionally, the weight ratio of sodium to calcium in the diluted gel is from 72:28 to 86:14. Further optionally, the weight ratio of sodium to calcium in the diluted gel that is essentially clear is from 80:20 to 86:14. Further optionally, the weight ratio of sodium to calcium in the diluted gel that is clear is from 81:19 to 86:14. Optionally, the weight ratio of sodium to calcium in the diluted gel is about 84:16.

Optionally, the diluted sodium calcium alginate gel is present in the composition in an amount of from 0.05 wt. % to 2 wt. %, based on the total weight of the oral care composition. Further optionally, the diluted sodium calcium alginate gel is present in the composition in an amount of from 0.1 wt. % to 1 wt. %, based on the total weight of the oral care composition. Further optionally, the diluted sodium calcium alginate gel is present in the composition in an amount of from 0.25 wt. % to 0.75 wt. %, based on the total weight of the oral care composition.

Optionally, the diluted sodium calcium alginate gel is present in the composition in an amount of about 0.17 wt. %, based on the total weight of the oral care composition.

Optionally, the diluted sodium calcium alginate gel is present in the composition in an amount of about 0.5 wt. %, based on the total weight of the oral care composition.

Optionally, the composition further comprises water in an amount of from 10 wt. % to 60 wt. %, based on the total weight of the oral care composition. Further optionally, the composition comprises water in an amount of from 15 wt. % to 55 wt. %, based on the total weight of the oral care composition. Further optionally, the composition comprises water in an amount of from 20 wt. % to 45 wt. %, based on the total weight of the oral care composition. Further optionally, the composition comprises water in an amount of from 25 wt. % to 35 wt. %, based on the total weight of the oral care composition. Still further optionally, the composition comprises water in an amount of from 28 wt. % to 32 wt. %, based on the total weight of the oral care composition.

Optionally, the ratio of water to the diluted sodium calcium alginate gel in the composition is from 80:1 to 180:1. Further optionally, the ratio of water to the diluted sodium calcium alginate gel in the composition is from 85:1 to 150:1. Further optionally, the ratio of water to the diluted sodium calcium alginate gel in the composition is from 90:1 to 120:1. Still further optionally, the ratio of water to the diluted sodium calcium alginate gel in the composition is from 95:1 to 105:1.

Optionally, the oral care composition further comprises one or more agents selected from diluents, bicarbonate salts, pH modifying agents, surfactants, foam modulators, additional thickening agents, humectants, sweeteners, flavorants, pigments, antibacterial agents, anticaries agents, fluoride ion sources, anticalculus or tartar control agents, and mixtures thereof.

Optionally, a humectant is present in an amount of from 35 wt. % to 60 wt. %, based on the total weight of the oral care composition. Further optionally, the humectant is present in an amount of from 42 wt. % to 53 wt. %, based on the total weight of the oral care composition. Still further optionally, the humectant is present in an amount of about 48 wt. %, based on the total weight of the oral care composition.

Optionally, the humectant is sorbitol.

Optionally, a humectant is present in an amount of from 0.5 wt. % to 2 wt. %, based on the total weight of the oral care composition. Further optionally, the humectant is present in an amount of from 0.7 wt. % to 1.5 wt. %, based on the total weight of the oral care composition. Still further optionally, the humectant is present in an amount of about 1.0 wt. %, based on the total weight of the oral care composition.

Optionally, the humectant is polyethylene glycol 600.

Optionally, a silica thickener is present in an amount of from 5 wt. % to 10 wt. %, based on the total weight of the oral care composition. Further optionally, the silica thickener is present in an amount of about 8 wt. %, based on the total weight of the oral care composition.

Optionally, the composition does not contain carboxymethylcellulose. Optionally, the composition does not contain cellulose polymers.

DETAILED DESCRIPTION

The following description of the preferred embodiments is merely exemplary in nature and is in no way intended to limit the invention, its application, or uses.

As used throughout, ranges are used as shorthand for describing each and every value that is within the range. Any value within the range can be selected as the terminus of the range.

All references cited herein are hereby incorporated by reference in their entireties. In the event of a conflict in a definition in the present disclosure and that of a cited reference, the present disclosure controls.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the term "about", when applied to the value for a parameter of a composition or method of this invention, indicates that the calculation or the measurement of the value allows some slight imprecision without having a substantial effect on the chemical or physical attributes of the composition or method. If, for some reason, the imprecision provided by "about" is not otherwise understood in the art with this ordinary meaning, then "about" as used herein indicates a possible variation of up to 5% in the value.

As referred to herein, all compositional percentages are by weight of the total composition unless otherwise indicated. As referred to herein, "ppm" (parts per million) refers to ppm by weight, unless otherwise indicated. As referred to herein, all ratios refer to weight ratios, unless otherwise indicated.

Unless otherwise indicated, all methods and examples disclosed herein were carried out at ambient temperature of 25° C.

The present inventors have found that, by using a combination of sodium alginate and calcium alginate as a rheology modifier, compositions having a clear, colourless appearance, desirable fluidity. Viscosity of sodium calcium alginate (in a ratio of sodium alginate to calcium alginate is 84:16 ranges from 1200-2000 cps at 1% aqueous solution, and excellent structural and thickening effects can be obtained. The ratio of sodium alginate to calcium alginate can be optimized so as to provide the desired rheological properties for the oral care compositions.

A first aspect of the present invention provides an oral care composition comprising a diluted sodium calcium alginate gel, wherein the oral care composition is a toothpaste, a gel, a mouthwash or a mouthrinse.

In some embodiments, the weight ratio of sodium to calcium in the diluted gel is from 72:28 to 95:5; from 75:25 to 92:8; from 78:22 to 90:10; from 80:20 to 88:12; or from 82:18 to 87:13. In some embodiments, the weight ratio of sodium to calcium in the diluted gel is about 84:16.

In some embodiments, the diluted sodium calcium alginate gel is present in the composition in an amount of from 0.05 wt. % to 2 wt. %; from 0.075 wt. % to 1.5 wt. %; from 0.1 wt. % to 1 wt. %; from 0.25 wt. % to 0.75 wt. %; or from 0.4 wt. % to 0.6 wt. %, based on the total weight of the oral care composition.

In some embodiments, the diluted sodium calcium alginate gel is present in the composition in an amount of from 0.1 wt. % to 0.5 wt. %, from 0.15 wt. % to 0.25 wt. %, or about 0.17 wt. %, based on the total weight of the oral care composition.

In some embodiments, the diluted sodium calcium alginate gel is present in the composition in an amount of about 0.5 wt. %, based on the total weight of the oral care composition.

In some embodiments, the oral care composition further comprises water. In some embodiments, the composition further comprises water in an amount of from 10 wt. % to 60 wt. %; from 15 wt. % to 55 wt. %; from 20 wt. % to 45 wt. %; from 25 wt. % to 35 wt. %; or from 28 wt. % to 32 wt. %, based on the total weight of the oral care composition. In some embodiments, the composition comprises water in an amount of about 51 wt. %, based on the total weight of the oral care composition. In some embodiments, the composition comprises water in an amount of about 30 wt. %, based on the total weight of the oral care composition. As described herein and unless otherwise indicated, references to the amount of water present in the composition includes free water which is added to the composition (e.g. as demineralized water), plus water which is introduced as part of another ingredient (for example, where a humectant is added to the composition as an aqueous solution).

In some embodiments, the ratio of water present in the composition to the diluted sodium calcium alginate gel present in the composition is from 80:1 to 180:1; from 85:1 to 150:1; from 90:1 to 120:1; or from 95:1 to 105:1. In some embodiments, the ratio of water present in the composition to the diluted sodium calcium alginate gel present in the composition is from 160:1 to 180:1; from 170:1 to 177:1; or about 175:1. In some embodiments, the ratio of water present in the composition to the diluted sodium calcium alginate gel present in the composition is about 102:1.

In some embodiments, free water (i.e. water which does not form part of another ingredient) is added to the composition in an amount of from 2 wt. % to 60 wt. %, from 3 wt. % to 35 wt. %, from 5 wt. % to 20 wt. %, from 7 wt. % to 15 wt. %, or from 8 wt. % to 10 wt. %, based on the total weight of the composition. In some embodiments, the ratio of free water (i.e. water which does not form part of another ingredient) to the diluted sodium calcium alginate gel present in the composition is from 45:1 to 70:1, from 50:1 to 65:1, from 52:1 to 60:1, or from 53:1 to 55:1.

In some embodiments, the oral care composition further comprises one or more agents selected from diluents, bicarbonate salts, pH modifying agents, surfactants, foam modulators, additional thickening agents, humectants, sweeteners, flavorants, pigments, antibacterial agents, anticaries agents, fluoride ion sources, anticalculus or tartar control agents, and mixtures thereof.

In some embodiments, the oral care compositions do not contain carboxymethyl cellulose. In some embodiments, the oral care compositions do not contain cellulose polymers.

In some embodiments, a humectant is present in the oral care composition in an amount of from 35 wt. % to 60 wt. %; from 39 wt. % to 55 wt. %; from 42 wt. % to 53 wt. %; from 46 wt. % to 49 wt. %; or about 48 wt. %, based on the total weight of the composition. In some embodiments, the humectant is sorbitol. In some embodiments, the humectant may be added to the composition as an aqueous solution, for example as a 70 wt. % solution of the humectant in water, in which case the amount of this humectant solution present in the oral care composition may be from 50 wt. % to 86 wt. %; from 56 wt. % to 79 wt. %; from 60 wt. % to 76 wt. %; from 66 wt. % to 70 wt. %; or about 68 wt. %, based on the total weight of the oral care composition. Sorbitol may be included in the compositions as a 70 wt. %.

In some embodiments, a humectant is present in the composition in an amount of from 0.5 wt. % to 2 wt. %; from 0.6 wt. % to 1.8 wt. %; from 0.7 wt. % to 1.5 wt. %; from 0.8 wt. % to 1.3 wt. %; or from 0.9 wt. % to 1.25 wt. %, based on the total weight of the oral care composition. In some embodiments, the humectant is present in an amount of about 1.0 wt. %, based on the total weight of the oral care composition. In some embodiments, the humectant is polyethylene glycol 600.

In some embodiments, a silica thickener is present in the composition in an amount of from 5 wt. % to 10 wt. %; from 6 wt. % to 9 wt. %; or from 7 wt. % to 8.5 wt %, based on the total weight of the oral care composition. In some embodiments, the silica thickener is present in an amount of about 8 wt. %, based on the total weight of the oral care composition. Silica thickeners which may be used in compositions of the present invention include, but are not limited to, silica DS 210 (available from Glassven)

In some embodiments, particularly (but not limited to) those embodiments where the composition is a toothpaste or a gel, the compositions of the present invention may further comprise an abrasive.

Abrasives that may be used include silica abrasives such as precipitated or hydrated silicas having a mean particle size of up to about 20 microns, such as Zeodent 105 and Zeodent 114 marketed by J.M. Huber Chemicals Division, Havre de Grace, Md. 21078, or Sylodent 783 marketed by Davison Chemical Division of W.R. Grace & Company. Other useful dentifrice abrasives include aluminium oxide, aluminum silicate, calcined alumina, bentonite or other siliceous materials, insoluble phosphates, calcium carbonate, and mixtures thereof. Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate.

The abrasive may be present in an amount of from 2 to 35 wt %; from 5 to 20 wt. %; or from 7 to 12 wt. % based on the weight of the composition. In some embodiments, the compositions of the present invention comprise an abrasive in an amount of about 8 wt. % based on the weight of the composition.

In some embodiments, the compositions of the invention comprise at least one surfactant. Any orally acceptable surfactant, most of which are anionic, nonionic or amphoteric, can be used. Suitable anionic surfactants include without limitation, water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable nonionic surfactants include without limitation, poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation, derivatives of $C_{8-20}$ aliphatic secondary and tertiary amines having an anionic group such as carboxylate, sulfate, sulfonate, phosphate or phosphonate. A suitable example is cocoamidopropyl betaine.

One or more surfactants are optionally present in a total amount of about 0.01 wt. % to about 10 wt. %, for example, from about 0.05 wt. % to about 5 wt. %, or from about 0.5 wt. % to about 4 wt. %, based on the total weight of the composition.

In some embodiments, the oral care composition further comprises a fluoride ion source. Suitable fluoride ion sources include, but are not limited to, stannous fluoride, sodium fluoride, potassium fluoride, potassium monofluorophosphate, sodium monofluorophosphate, ammonium monofluorophosphate, sodium fluorosilicate, ammonium fluorosilicate, an amine fluoride, ammonium fluoride, and combinations thereof. Fluoride ion sources may be present at a level of from 0.001 wt. % to 10 wt. %, from 0.003 wt. % to 5 wt. %, from 0.01 wt. % to 1 wt. %, or from 0.50 wt. % to 0.80 wt. % based on the total weight of the composition.

The composition of the present invention may additionally optionally comprise a tartar control (anticalculus) agent as provided below. Tartar control agents among those useful herein include salts of the specified agents, including alkali metal and ammonium salts. The agents include: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof.

In some embodiments, the compositions of the present invention comprise at least one sweetener, useful for example to enhance taste of the composition. Any orally acceptable natural or artificial sweetener can be used, including without limitation dextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, mannitol, xylitol, maltitol, isomalt, aspartame, neotame, saccharin and salts thereof, dipeptide-based intense sweeteners, cyclamates and the like. An example of a sweetener which may be used in compositions of the present invention is sodium saccharin.

One or more sweeteners may be present in a total amount depending strongly on the particular sweetener(s) selected, but typically from 0.005 wt. % to 5 wt. %, by total weight of the composition, optionally from 0.01 wt. % to 2.5 wt. %, further optionally from 0.05 wt. % to 1.0 wt. %, further optionally from 0.1 to 0.5 wt. %, further optionally from 0.2 to 0.3 wt. %, based on the total weight of the composition.

In some embodiments, compositions of the present invention comprise at least one flavorant, useful for example to enhance taste of the composition. Any orally acceptable natural or synthetic flavorant can be used, including without limitation vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Other possible flavorants include FC Brighter Flavor K91-5661, a Colgate-Palmolive compound flavour. Also encompassed within flavorants herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like.

One or more flavorants are optionally present in a total amount of from about 0.01 wt. % to about 5 wt. %, for example, from about 0.05 wt. % to about 2.5 wt. %, optionally about 0.1 wt. % to about 1.5 wt. %, further optionally about 0.5 wt. % to about 1.3 wt. %, further optionally from about 1.0 wt. % to 1.2 wt. %, based on the total weight of the composition.

Oral care compositions of the invention may comprise at least one colorant. Colorants herein include pigments, dyes, lakes and agents imparting a particular luster or reflectivity such as pearling agents. Any orally acceptable colorant can be used, including without limitation talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride and the like. Other possible colorants include D&C yellow #10 and Blue #15 marketed by BASF.

One or more colorants are optionally present in a total amount of from about 0.0001 wt. % to about 5 wt. %, optionally from about 0.0005 wt. % to about 1 wt. %, optionally from about 0.001 wt % to about 0.005 wt. % by total weight of the composition.

In some embodiments, the oral care compositions of the present invention comprise at least one bicarbonate salt, useful for example to impart a "clean feel" to teeth and gums due to effervescence and release of carbon dioxide. Any orally acceptable bicarbonate can be used, including without limitation, alkali metal bicarbonates such as sodium and potassium bicarbonates, ammonium bicarbonate and the like. One or more bicarbonate salts are optionally present in a total amount of about 0.1 wt. % to about 50 wt. %, for example about 1 wt. % to 20 wt. %, by total weight of the composition.

The compositions of the present invention optionally comprise an antibacterial or preservative agent, such as chlorhexidine, triclosan, quaternary ammonium compounds (for example benzalkonium chloride) or parabens such as methylparaben or propylparaben. One or more antibacterial or preservative agent is optionally present in the composition in a total amount of from about 0.01 wt. % to about 0.5 wt. %, optionally about 0.05 wt. % to about 0.1 wt. % by total weight of the composition.

The composition of the present invention optionally comprises a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

The composition of the present invention optionally incorporates one or more antisensitivity agents, e.g., potassium salts such as potassium nitrate, potassium bicarbonate, potassium chloride, potassium citrate, and potassium oxalate; capsaicin; eugenol; strontium salts; zinc salts; chloride salts and combinations thereof. Such agents may be added in effective amounts, e.g., from about 1 wt. % to about 20 wt. % by weight based on the total weight of the composition, depending on the agent chosen. The compositions of the present invention may also be used to treat hypersensitivity by blocking dentin tubules when applied to a tooth.

In some embodiments, the composition of the invention further comprises an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

In some embodiments, the compositions of the present invention comprise at least one pH modifying agent. Such agents include acidifying agents to lower pH, basifying agents to raise pH, and buffering agents to control pH within a desired range. For example, one or more compounds selected from acidifying, basifying and buffering agents can be included to provide a pH of 2 to 10, or in various illustrative embodiments, 2 to 8, 3 to 9, 4 to 8, 5 to 7, 6 to 10, 7 to 9, etc. Any orally acceptable pH modifying agent can be used, including without limitation, carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate), imidazole and the like. One or more pH modifying agents are optionally present in a total amount effective to maintain the composition in an orally acceptable pH range.

EXAMPLES

Gel Slurries

A gel slurry was prepared using the following ingredients:

TABLE 1

| Ingredient | Amount (wt. %) |
| --- | --- |
| Sorbitol - non-crystallizing (70 wt. % aqueous solution) | 68.000 |
| Polyethylene glycol 600 | 1.000 |
| Diluted Sodium calcium alginate gel | 0.500 |
| Demineralized water | 30.500 |

The diluted sodium calcium alginate gel was dispersed in polyethylene glycol 600 as a gum slurry. The diluted gel could either be premixed with PEG 600 or directly dispersed and swelled into water. Premixing with PEG 600 promotes a more rapid dispersion but it depends on the formula dosage of PEG 600. In some formula there is very low level of PEG 600. The sorbitol was added to a gel tank, and the gum slurry was then added to the gel tank and allowed to mix for 10 minutes. The demineralized water was then added, the temperature increased to 55° C., and the mixture was allowed to mix for 20 minutes.

Gel slurries as in Table 1 were prepared using various ratios of sodium alginate to calcium alginate, and their appearance, colour, fluidity and viscosity were analysed. The results are shown in table 2, below:

TABLE 2

| | Ratio of sodium:calcium in the alginate gel | | | | |
| --- | --- | --- | --- | --- | --- |
| | 87:13 | 86:14 | 84:16 | 80:20 | 78:22 |
| Appearance | Clear | Clear | Clear | Clear | clear |
| Colour | Colourless | Colourless | Colourless | Slight yellowish | Yellowish |
| Fluidity | Good | Good | Good | Good | Good |
| Viscosity | 610 cps | 720 cps | 870 cps | 910 cps | 950 cps |

Viscosities were measured by Brookfield Programmable D-II+ Viscometer, with 2# Spindle at 50 rpm (below 800 cps) and #2 spindle 20 rpm (between 800-200 rpm).

As can be seen from Table 2, all of these ratios of sodium:calcium in the alginate gel gave clear slurries with good fluidity, and the gel slurries with a ratio of 87:13 or 84:16 sodium:calcium alginate gel were colourless. The appearance of these gel slurries is clear.

The gel slurries having a range of ratios from 86:14 to 80:20 of sodium:calcium alginate gel was selected as having the most desirable properties for clarity and have parity initial viscosity as control formula.

Toothpastes

A prototype toothpaste formulation was prepared using the following ingredients.

TABLE 3

| Ingredient | Amount (wt. %) |
|---|---|
| Sorbitol - non-crystallizing (70 wt. % solution) | 68.000 |
| Sodium saccharin | 0.270 |
| Sodium monofluorophosphate | 0.760 |
| Polyethylene glycol 600 | 1.000 |
| Diluted sodium calcium alginate gel | 0.170 |
| Thickener silica DS 210 | 8.000 |
| Silica Zeodent 114 | 8.000 |
| 95% sodium lauryl sulfate - granules | 2.300 |
| FC brighter flavor K91-5561 | 1.150 |
| Cocoamidopropyl betaine | 1.250 |
| D&C Yellow #10 | 0.00005 |
| Blue #15 | 0.00140 |
| Demineralized water | 9.099 |

To make a gel slurry, the diluted sodium calcium alginate gel was dispersed in polyethylene glycol 600 as a gum slurry. The sorbitol was added to a gel tank, and the sodium monofluorophosphate, sodium saccharin and colourants were added to the sorbitol and allowed to mix for 5 minutes. The gum slurry was then added to the gel tank and allowed to mix for 10 minutes. The demineralized water was then added, the temperature increased to 55° C., and the mixture was allowed to mix for 20 minutes. To make the toothpaste, the gel slurry was transferred to a paste tank and deaerated for 2 minutes at full vacuum. Vacuum is set at −0.090 MPa with agitation/homogenous set at 75/1850 rpm respectively. Silica was then added under vacuum at −0.090 MPa and agitation/homogenous of 75/1850 rpm. The mixture is mixed for 10 minutes, after which the paste was checked of white lumps. If lumps are present, the mixture is mixed additionally at agitation/homogenous of 75/1850 rpm for additional 5 minutes. The flavorant was then added and the mixture was mixed for 3 minutes at 46° C. under vacuum. Sodium lauryl sulfate was then added mixed for 3 minutes. The betaine was then added and mixed for 10 minutes under full vacuum until homogenous. The maximum vacuum was −0.090 MPa.

Prototype toothpastes containing various ratios of sodium:calcium in a 0.17% diluted alginate gel and 8 wt. % thickener silica (free of carboxymethyl cellulose) were prepared. A control system was prepared using a gum and thickening system including CMC. The viscosities of these toothpastes were measured at various times after their preparation, and were compared against a control which contained 0.5 wt. % carboxymethyl cellulose and 8 wt. % thickener silica. Initial viscosity was measured under around 30' C. Others were measured at 25' C. The results are shown in Table 4, below:

TABLE 4

| | | Ratio of sodium:calcium in the alginate gel | | |
|---|---|---|---|---|
| | Control 0.5 wt. % CMC; 8 wt. % | 87:13 0 wt. % CMC; 0.17 wt % sodium alginate/calcium alginate; 8 wt. % thickener silica | 84:16 | 78:22 |
| Sample Aging | thickener silica Viscosity (×$10^4$ cps) | Viscosity (×$10^4$ cps) | Viscosity (×$10^4$ cps) | Viscosity (×$10^4$ cps) |
| Initial | 12.1 | 9.2 | 13.6 | 13.4 |
| 1 hr | 16.1 | 9.9 | 15.3 | 15.4 |
| 2 hr | 18.3 | 12.5 | 18.9 | 19.6 |
| 3 hr | 19.3 | 12.5 | — | — |
| 1 day | — | 15.9 | 19.2 | — |
| 2 day | — | — | 19.8 | — |
| 3 day | 26.2 | 17.9 | — | 18.8 |
| 1 week | 34.1 | 20.0 | 25.6 | 24.9 |

It can be seen from the above data that the compositions containing the diluted sodium calcium alginate gel provided a viscosity level similar to control and showed a smaller increase in viscosity upon aging than observed for the control. The initial viscosity of formula with sodium alginate:calcium alginate at 84:16 matches the initial viscosity of control. The 78:22 ratio also matches initial viscosity, but the clarity was not as good as control.

Whilst particular embodiments of the invention have been illustrated and described, it will be clear to those skilled in the art that various changes and modifications may be made without departing from the scope of the invention as defined in the appended claims.

The invention claimed is:

1. An oral care composition comprising a diluted sodium calcium alginate gel, wherein the oral care composition is a toothpaste, a gel, a mouthwash or a mouthrinse;
    wherein the weight ratio of sodium to calcium in the diluted gel is from 80:20 to 86:14, and
    wherein the diluted sodium calcium alginate gel is present in the composition in an amount of about 0.17 wt. %, based on the total weight of the oral care composition; and further comprises water in an amount of from 10 wt. % to 60 wt. %, based on the total weight of the oral care composition.

2. The oral care composition of claim 1, wherein the composition is a toothpaste or a gel.

3. The oral care composition of claim 1, wherein the weight ratio of sodium to calcium in the diluted gel is from 81:19 to 86:14.

4. The oral care composition of claim 3, wherein the weight ratio of sodium to calcium in the diluted gel is about 84:16.

5. The oral care composition of claim 1, wherein the composition comprises water in an amount of from 15 wt. % to 55 wt. %, based on the total weight of the oral care composition.

6. The oral care composition of claim 5, wherein the composition comprises water in an amount of from 20 wt. % to 45 wt. %, based on the total weight of the oral care composition.

7. The oral care composition of claim 6, wherein the composition comprises water in an amount of from 25 wt. % to 35 wt. %, based on the total weight of the oral care composition.

8. The oral care composition of claim 7, wherein the composition comprises water in an amount of from 28 wt. % to 32 wt. %, based on the total weight of the oral care composition.

9. The oral care composition of claim 1, wherein the ratio of water to the diluted sodium calcium alginate gel in the composition is from 80:1 to 180:1.

10. The oral care composition of claim 9, wherein the ratio of water to the diluted sodium calcium alginate gel in the composition is from 85:1 to 150:1.

11. The oral care composition of claim 10, wherein the ratio of water to the diluted sodium calcium alginate gel in the composition is from 90:1 to 120:1.

12. The oral care composition of claim 11, wherein the ratio of water to the diluted sodium calcium alginate gel in the composition is from 95:1 to 105:1.

13. The oral care composition of claim 1, further comprising one or more agents selected from diluents, bicarbonate salts, pH modifying agents, surfactants, foam modulators, additional thickening agents, humectants, sweeteners, flavorants, pigments, antibacterial agents, anticaries agents, fluoride ion sources, anticalculus or tartar control agents, and mixtures thereof.

14. The oral care composition of claim 13, wherein a humectant is present in an amount of from 35 wt. % to 60 wt. %, based on the total weight of the oral care composition.

15. The oral care composition of claim 14, wherein the humectant is present in an amount of from 42 wt. % to 53 wt. %, based on the total weight of the oral care composition.

16. The oral care composition of claim 15, wherein the humectant is present in an amount of about 48 wt. %, based on the total weight of the oral care composition.

17. The oral care composition of claim 13, wherein the humectant is sorbitol.

18. The oral care composition of claim 13, wherein a humectant is present in an amount of from 0.5 wt. % to 2 wt. %, based on the total weight of the oral care composition.

19. The oral care composition of claim 18, wherein the humectant is present in an amount of from 0.7 wt. % to 1.5 wt. %, based on the total weight of the oral care composition.

20. The oral care composition of claim 19, wherein the humectant is present in an amount of about 1.0 wt. %, based on the total weight of the oral care composition.

21. The oral care composition of claim 18, wherein the humectant is polyethylene glycol 600.

22. The oral care composition of claim 12, wherein a silica thickener is present in an amount of from 5 wt. % to 10 wt. %, based on the total weight of the oral care composition.

23. The oral care composition of claim 22, wherein the silica thickener is present in an amount of about 8 wt. %, based on the total weight of the oral care composition.

24. The oral care composition of claim 1, wherein the composition does not contain carboxymethylcellulose.

25. The oral care composition of claim 1, wherein the composition does not contain cellulose polymers.

* * * * *